United States Patent
Kang et al.

(10) Patent No.: US 12,193,828 B2
(45) Date of Patent: *Jan. 14, 2025

(54) APPARATUS AND METHOD FOR MONITORING A DRIVER WITH EPILEPSY USING BRAIN WAVES

(71) Applicants: HYUNDAI MOTOR COMPANY, Seoul (KR); KIA CORPORATION, Seoul (KR); SOOKMYUNG WOMEN'S UNIVERSITY INDUSTRY-ACADEMIC COOPERATION FOUNDATION, Seoul (KR)

(72) Inventors: Jeong Su Kang, Seongnam-si (KR); Suh Yeon Dong, Seoul (KR)

(73) Assignees: HYUNDAI MOTOR COMPANY, Seoul (KR); KIA CORPORATION, Seoul (KR); SOOKMYUNG WOMEN'S UNIVERSITY INDUSTRY—ACADEMIC COOPERATION FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/244,092

(22) Filed: Sep. 8, 2023

(65) Prior Publication Data
US 2023/0414162 A1 Dec. 28, 2023

Related U.S. Application Data

(63) Continuation of application No. 17/028,252, filed on Sep. 22, 2020, now Pat. No. 11,806,157.

(30) Foreign Application Priority Data

Nov. 28, 2019 (KR) .................. 10-2019-0155403

(51) Int. Cl.
*A61B 5/00* (2006.01)
*A61B 5/18* (2006.01)
(Continued)

(52) U.S. Cl.
CPC .............. *A61B 5/4094* (2013.01); *A61B 5/18* (2013.01); *A61B 5/374* (2021.01); *A61B 5/7264* (2013.01)

(58) Field of Classification Search
None
See application file for complete search history.

(56) References Cited

U.S. PATENT DOCUMENTS

| 10,007,263 B1 | 6/2018 | Fields et al. |
| 2003/0199781 A1 | 10/2003 | Tsuboshita |

(Continued)

FOREIGN PATENT DOCUMENTS

| JP | 2003310564 A | 11/2003 |
| JP | 2019199177 A | 11/2019 |

(Continued)

*Primary Examiner* — Etsub D Berhanu
(74) *Attorney, Agent, or Firm* — Lempia Summerfield Katz LLC

(57) ABSTRACT

An apparatus and method for monitoring a driver using a brain wave signal of the driver are disclosed. The monitoring method includes collecting a brain wave signal for a driver in a vehicle for a predetermined time, determining the driver's state by analyzing the brain wave signal collected for the predetermined time, and controlling an operation of the vehicle on the basis of the determined driver's state.

16 Claims, 9 Drawing Sheets

(51) Int. Cl.
    *A61B 5/372*     (2021.01)
    *A61B 5/374*     (2021.01)
    *G06F 3/01*     (2006.01)

(56) References Cited

U.S. PATENT DOCUMENTS

| | | |
|---|---|---|
| 2004/0077967 A1 | 4/2004 | Jordan |
| 2006/0011399 A1 | 1/2006 | Brockway et al. |
| 2006/0094974 A1 | 5/2006 | Cain |
| 2006/0111644 A1 | 5/2006 | Guttag et al. |
| 2007/0249954 A1 | 10/2007 | Virag et al. |
| 2013/0096391 A1 | 4/2013 | Osorio et al. |
| 2014/0276090 A1 | 9/2014 | Breed |
| 2019/0092337 A1 | 3/2019 | Chua et al. |
| 2019/0161091 A1 | 5/2019 | An |

FOREIGN PATENT DOCUMENTS

| | | |
|---|---|---|
| KR | 20140119315 A | 10/2014 |
| KR | 20150029969 A | 3/2015 |
| KR | 20190111570 A | 10/2019 |

FIG. 4A
FIG. 4B
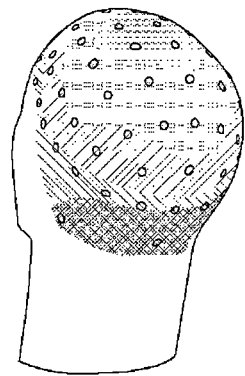
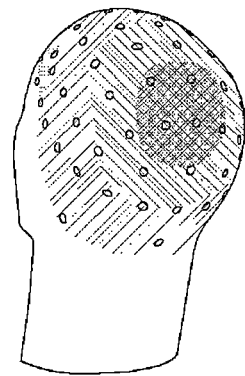
−9.3µN    −0.6µN
−1.8µN    13.0µN

APPARATUS AND METHOD FOR MONITORING A DRIVER WITH EPILEPSY USING BRAIN WAVES

CROSS REFERENCE TO RELATED APPLICATION

This application is a continuation of U.S. patent application Ser. No. 17/028,252 filed Sep. 22, 2020, which claims priority to and the benefit of Korean Patent Application No. 10-2019-0155403, filed Nov. 28, 2019, which is incorporated herein by reference in its entirety.

TECHNICAL FIELD

The present disclosure relates to a mobility or vehicle controlling method and apparatus. More particularly, the present disclosure relates to a mobility or vehicle controlling method and apparatus based on error monitoring.

BACKGROUND

The statements in this section merely provide background information related to the present disclosure and may not constitute prior art.

As one of the transport means, a vehicle (i.e., a mobility device or a mobility) is a very important means and tool for living a life in the modern world. Furthermore, a vehicle itself may be regarded as something special that gives meaning to someone.

As technology is advanced, functions provided by a vehicle also gradually evolve. For example, in recent years, vehicles not only transport a passenger to a destination, but also meet a passenger's needs for faster and safer travel to a destination. In addition, new devices are being added to a vehicle system in order to satisfy a passenger's aesthetic taste and comfort. In addition, the existing devices like steering wheels, transmissions, and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

An object of the present disclosure is to provide an apparatus and method for monitoring a driver on the basis of the driver's brain wave signals.

Another object of the present disclosure is to provide a monitoring apparatus and method for monitoring a driver with epilepsy that controls a mobility or vehicle by determining a driver's state on the basis of the driver's brain wave signal.

The technical objects of the present disclosure are not limited to the above-mentioned technical objects. Other technical objects that are not mentioned should be clearly understood by those having ordinary skill in the art through the following descriptions.

According to the present disclosure, an apparatus for monitoring a driver using a brain wave signal of the driver may be provided. The apparatus may include a sensor configured to collect a brain wave signal for a driver in a vehicle for a predetermined time. The apparatus may further include an analyzer configured to determine the driver's state by analyzing the brain wave signal collected for the predetermined time. The apparatus may further a controller configured to control an operation of the vehicle on the basis of the determined driver's state.

The brain wave signal may be a brain wave signal in a time series plane.

The brain wave signal may be a brain wave signal according to frequency.

The analysis may include a process of comparing an amplitude of the brain wave signal, which is collected for the predetermined time, and a predetermined threshold.

The analysis may include a process of comparing an amplitude of a power spectrum of the brain wave signal at each frequency, which is collected for the predetermined time, and a predetermined threshold.

The threshold may be a value obtained based on a learning model that is implemented for at least one of a brain wave signal during the driver's normal state, a brain wave signal during the driver's seizure, and/or a brain wave signal during a seizure of predetermined epilepsy patients.

The obtained value may be an amplitude or a power spectrum value of a brain wave signal.

The driver's state may be classified as a predetermined phase on the basis of at least one of a normal state or a seizure.

The driver's state may be determined based on a ratio of a brain wave signal collected for the predetermined time to a brain wave signal during the driver's normal state.

The brain wave signal may be an amplitude or a power spectrum value of the brain wave signal.

The driver's state may be classified into multiple phases on the basis of the ratio.

The ratio may be a value set for monitoring the driver's state.

The driver's state may be determined based on a ratio of a brain wave signal collected for the predetermined time to a brain wave signal during the driver's seizure.

The driver's state may be classified into multiple phases on the basis of the ratio.

The analysis may be performed by using a brain wave signal template for each driver.

The controller may limit at least one of speed, power, and/or torque of the vehicle to a predetermined value and below on the basis of the determined driver's state.

The controller may transmit current location information of the vehicle to at least one of a preset user and/or a preset place on the basis of the determined state of the driver.

The controller may stop the vehicle on the basis of the determined driver's state.

When the driver's state changes to a normal state, the controller may turn off the operation of limiting the speed of the vehicle.

In addition, according to the present disclosure, a method for monitoring a driver using a brain wave signal may be provided. The method may include collecting a brain wave signal for a driver in a vehicle for a predetermined time; determining the driver's state by analyzing the brain wave signal collected for the predetermined time; and controlling an operation of the vehicle on the basis of the determined driver's state.

The brain wave signal may be a brain wave signal in a time series plane.

The brain wave signal may be a brain wave signal according to frequency.

The analysis may include a process of comparing an amplitude of the brain wave signal, which is collected for the predetermined time, and a predetermined threshold.

The analysis may include a process of comparing an amplitude of a power spectrum of the brain wave signal at each frequency, which is collected for the predetermined time, and a predetermined threshold.

The threshold may be a value obtained based on a learning model that is implemented for at least one of a brain wave signal during the driver's normal state, a brain wave signal during the driver's seizure, and/or a brain wave signal during a seizure of predetermined epilepsy patients.

The obtained value may be an amplitude or a power spectrum value of a brain wave signal.

The driver's state may be classified as a predetermined phase on the basis of at least one of a normal state or a seizure.

The driver's state may be determined based on a ratio of a brain wave signal collected for the predetermined time to a brain wave signal during the driver's normal state.

The driver's state may be classified into multiple phases on the basis of the ratio.

The driver's state may be determined based on a ratio of a brain wave signal collected for the predetermined time to a brain wave signal during the driver's seizure.

The brain wave signal may be an amplitude or a power spectrum value of the brain wave signal.

The driver's state may be classified into multiple phases on the basis of the ratio.

The ratio may be a value set for monitoring the driver's state.

The analysis may be performed by using a brain wave signal template for each driver.

The controlling of an operation of the vehicle may limit at least one of speed, power, and/or torque of the vehicle to a predetermined value and below on the basis of the determined driver's state.

The controlling of an operation of the vehicle may transmit location information of the vehicle to at least one of a preset user and/or a preset place on the basis of the determined state of the driver.

The controlling of an operation of the vehicle may stop the vehicle on the basis of the determined driver's state.

When the driver's state changes to a normal state, the controlling of an operation of the vehicle may turn off the operation of limiting the speed of the vehicle.

The features briefly summarized above regarding the present disclosure are merely specific aspects of the detailed description below of the present disclosure and do not limit the scope of the present disclosure.

According to the present disclosure, an apparatus and method for monitoring a driver on the basis of the driver's brain wave signal may be provided.

In addition, according to the present disclosure, a monitoring apparatus and method may be provided, which control a mobility or vehicle by determining a driver's state on the basis of the driver's brain wave signal.

Effects expected from the present disclosure are not limited to the above-mentioned effects, and other effects not mentioned above may be clearly understood by those having ordinary skill in the art from the following description.

BRIEF DESCRIPTION OF THE DRAWINGS

In order that the disclosure may be well understood, various forms of the disclosure are now described, given by way of example, with reference to the accompanying drawings, in which:

FIGS. 4A and 4B are views respectively illustrating measurement areas of ERP and Pe in one form of the present disclosure;

DETAILED DESCRIPTION

Figure 1:
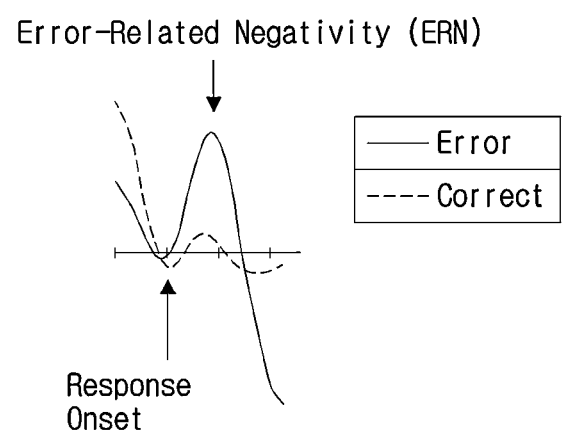
FIG. 1 is a view illustrating a general waveform of Error-Related Negativity (ERN) in one form of the present disclosure.

The following description is merely exemplary in nature and is not intended to limit the present disclosure, application, or uses. It should be understood that throughout the drawings, corresponding reference numerals indicate equivalent or corresponding parts and features.

Specific forms of the present disclosure are described in detail such that those having ordinary skill in the art would easily understand and implement an apparatus and a method provided by the present disclosure in conjunction with the accompanying drawings. However, the present disclosure may be embodied in various forms and the scope of the present disclosure should not be construed as being limited to the specific forms.

In describing forms of the present disclosure, well-known functions or constructions are not described in detail when they may obscure the spirit of the present disclosure.

In the present disclosure, it should be understood that when an element is referred to as being "connected to", "coupled to", or "combined with" another element, it can be directly connected or coupled to or combined with the other element or intervening elements may be present therebetween. It should be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It should be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. In other words, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner. When a unit, module, component, device, element, or the like of the present disclosure is described as having a purpose or performing an operation, function, or the like, the unit, module, component, device, or element should be considered herein as being "configured to" meet that purpose or to perform that operation or function. Further, the controller described herein may include a processor programmed to perform the noted operation, function, operation, or the like.

In the present disclosure, all of the constituent elements described in various forms should not be construed as being essential elements but some of the constituent elements may be optional elements. Accordingly, forms configured by respective subsets of constituent elements in a certain form also may fall within the scope of the present disclosure. In addition, forms configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. A research on interface control using a brain wave signal according to a person's intention is under way. A brain wave signal may be obtained by using EEG (Electro Encephalography) using electrical signals caused by brain activities, MEG (Magneto Encephalography) using magnetic signals occurring with electrical signals, and fMRI (functional Magnetic Resonance Imaging) or fNIRS (Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (Power spectrum classification). The classification considers a measured brain wave signal as a linear sum of simple signals at each specific frequency, decomposes the signal into each frequency component, and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 μV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz, and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of head. The cerebral cortex may be divided into frontal cortex, parietal cortex, temporal cortex, and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (i.e., image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, i.e., a brain activity commonly associated with stimulus processing.

As ERP has a high time resolution, it is closely related to a research on cognitive function. ERP is an electrical phenomenon that is evoked by an external stimulus or is related to an internal state. According to types of stimuli, ERPs may be classified into auditory sense-related potentials, sight-related potentials, somatic sense-related potentials, and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs are described.

For example, N100 is related to a response to an unpredictable stimulus.

MMN (Mismatch Negativity) may be generated not only by a focused stimulus but also by non-focused stimulus. MMN may be used as an indicator for whether or not a sense memory (echoic memory) operates before initial attention. P300, which is described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search, and alleviation of uncertain feeling and is related to perceptual decision distinguishing stimuli from outside. As the generation of P300 is related to a cognitive function, P300 is generated irrespective of types of presented stimuli. For example, P300 may be generated in auditory stimuli, visual stimuli, and somatic stimuli. P300 is widely applied to a research on brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. In one embodiment, when a subject cognizes a mistake or an error, ERN is generated and its negative peak appears mainly in the frontal and central zones for about 50~150 ms. More specifically, it may appear in a situation where a mistake related to motor response is likely to occur and may also be used to indicate a negative self-judgment.

Hereinafter, the major features of ERN are described in more detail.

FIG. 1 is a view illustrating a general waveform of ERN according to one form of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated and has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (i.e., Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

In addition, as a larger peak value of ERN is obtained, it may be considered as reflecting a more serious mistake or error.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe are described in more detail.

Figure 2:
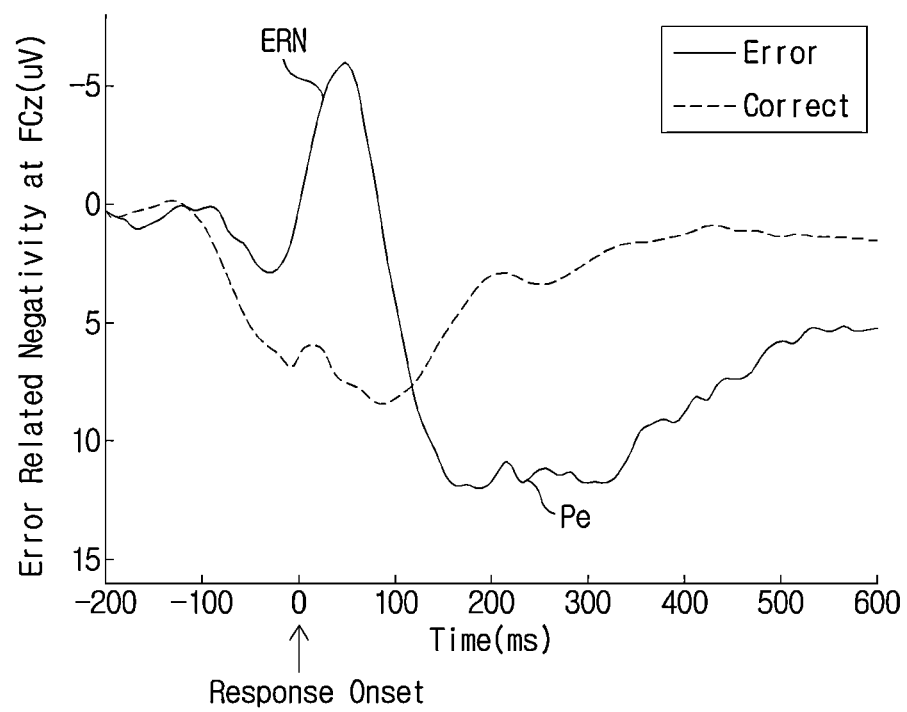
FIG. 2 is a view illustrating general waveforms of ERN and Error Positivity (Pe) according to one form of the present disclosure.

FIG. 2 is a view illustrating general waveforms of ERN and Pe according to another form of the present disclosure.

Referring to FIG. 2, negative potential values are depicted above positive potential values. In addition, it can be confirmed that an ERP with a negative peak value, i.e., an ERN is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, i.e., a Pe is generated within a second predetermined time range after the onset of the ERN. In addition, the second predetermined time range may be about 150~300 ms after an error onset. Alternatively, the second predetermined time range may mean about 200~400 ms.

Figure 3:
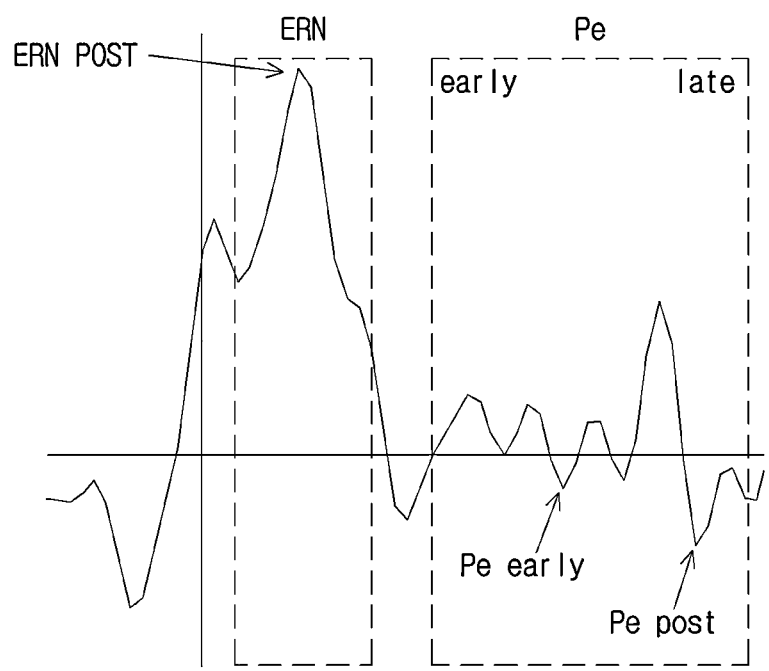
FIG. 3 is a view illustrating a deflection characteristic of Pe according to another form of the present disclosure.

FIG. 3 is a view illustrating a deflection characteristic of Pe in one form of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

FIGS. 4A and 4B are views illustrating measurement areas of ERP and Pe according to one form of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (i.e., FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
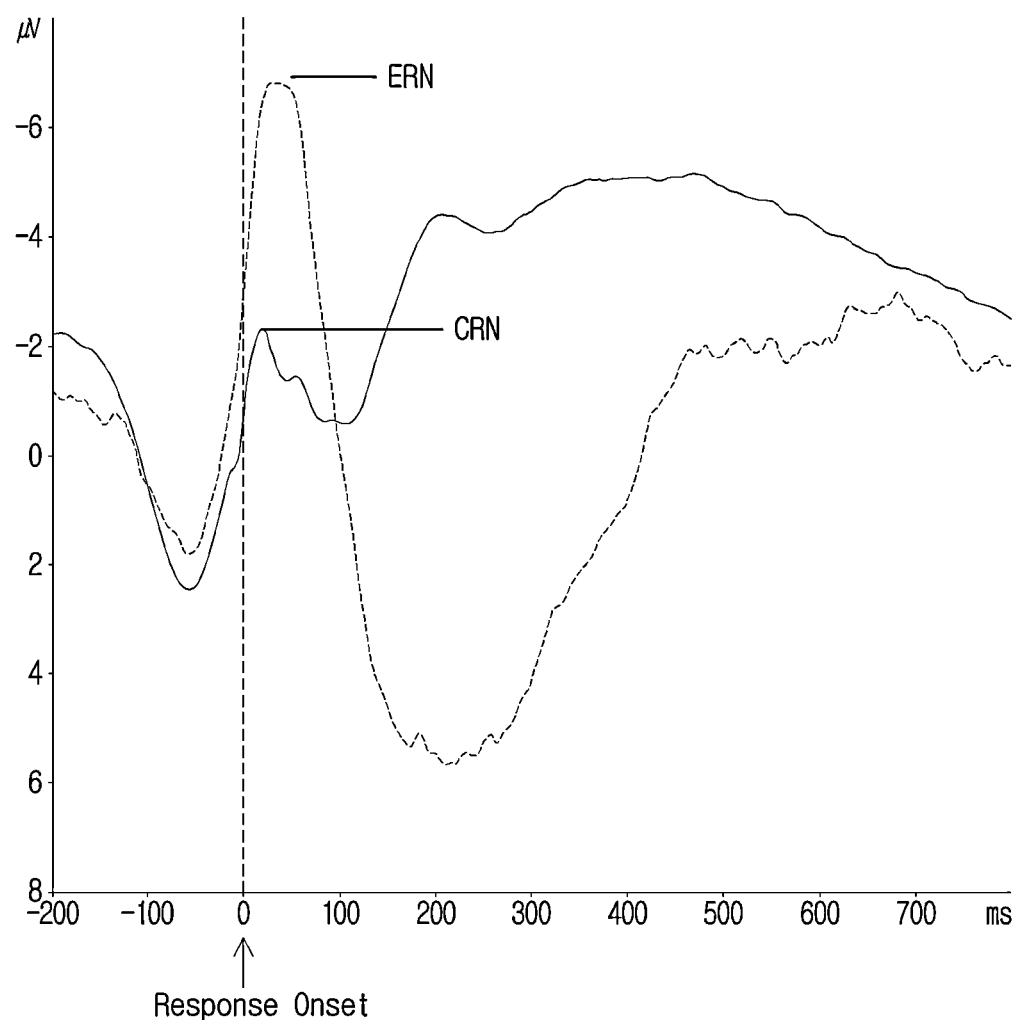
FIG. 5 is a view illustrating general waveforms of ERN and CRN according to one form of the present disclosure.

For yet another example, CRN (Correct-Related Negativity) is an ERP generated by a correct trial and is a negative value that is smaller than ERN. Like ERN, CRN may be generated in the initial latent period (i.e., 0~100 ms). FIG. 5 is a view illustrating general waveforms of ERN and CRN in one form of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushed a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
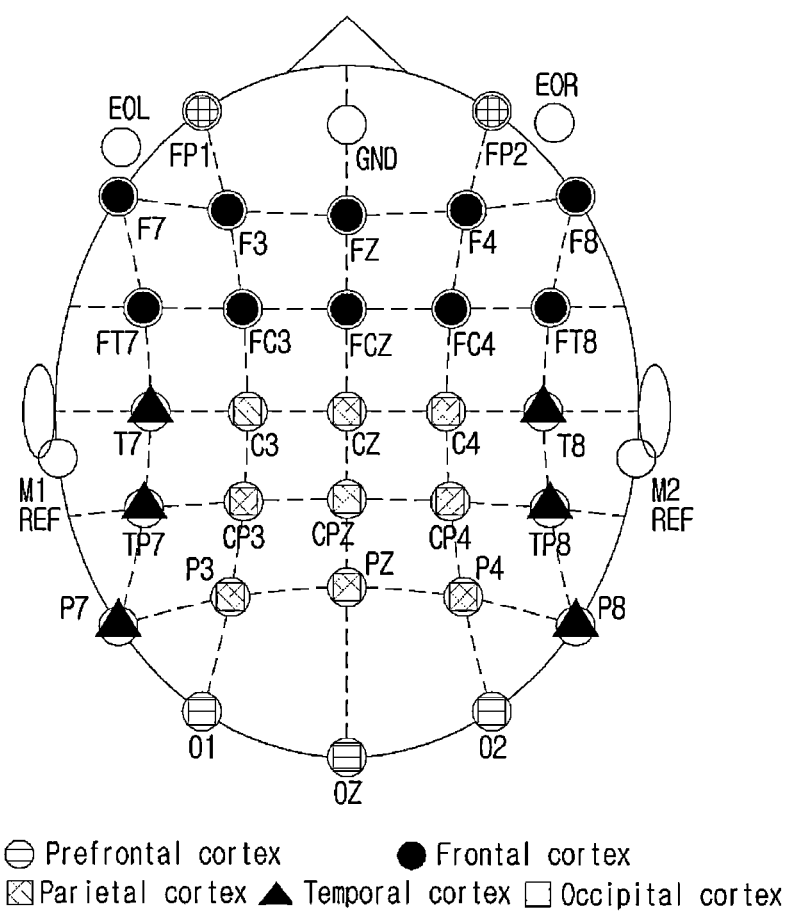
FIG. 6 is a view illustrating EEG measurement channels corresponding to cerebral cortex areas in one form of the present disclosure.

FIG. 6 is a view illustrating EEG measurement channels corresponding to the cerebral cortex areas according to one form of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
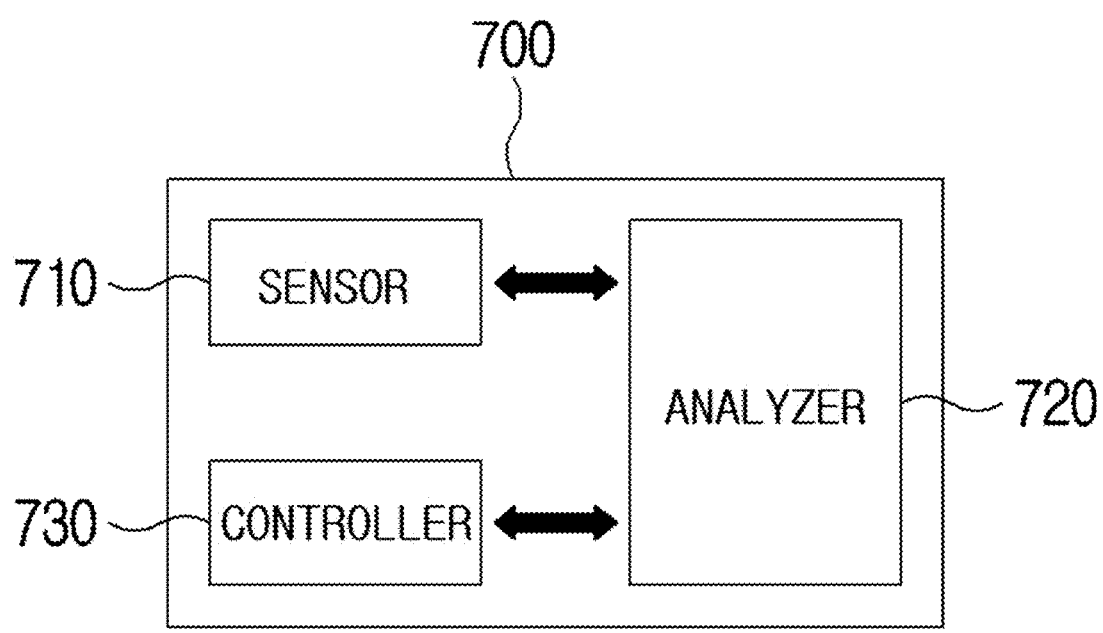
FIG. 7 is a block diagram illustrating a configuration of an apparatus for monitoring a driver with epilepsy on the basis of the driver's brain wave signal according to one embodiment of the present disclosure.

FIG. 7 is a block diagram illustrating a configuration of an apparatus for monitoring a driver with epilepsy on the basis of the driver's brain wave signal according to one embodiment of the present disclosure.

Epilepsy is a brain disorder in which nerve cells in the brain cause temporary abnormality and the consequential excitement is so excessive that brain functions are temporarily paralyzed while being accompanied by the loss of consciousness, seizures, or abnormal behaviors, and such convulsions occur chronically and recurrently.

Since driving may significantly affect not only the driver but also others, epileptic conditions are generally recognized as a ground for disqualification from driving. However, driving is not immediately prohibited on the ground of epileptic conditions, and an epilepsy patient is eligible to obtain a driver's license as long as the patient satisfies certain requirements specified by the Road Traffic Act and the Enforcement Ordinance of the Road Traffic Act.

As determining symptoms and first aid treatment are critical to epilepsy, the state of a driver with epilepsy needs to be monitored and determined while the driver is operating a mobility.

Meanwhile, although no epileptic seizure recurrently occurs, if a pathological change that is likely to cause epilepsy is found by brain scanning or other similar methods, such a change may be classified as epilepsy. In addition, although there is no typical symptom like seizure, seemingly minor symptoms like spacing out, late reaction, a partial fit like shaking one arm, getting goose bumps, or vomiting may also be classified as epilepsy. In addition, even when no epileptic wave (seizure wave) is detected in an electroencephalogram (EEG) test for diagnosing epilepsy, it may be a hasty conclusion that the subject is free of epilepsy. In other words, no epileptic seizure wave may be detected from a person with epilepsy.

Meanwhile, it is known that the brain wave signals of epilepsy patients without seizures can be distinguished from the brain wave signals of normal people. In other words, even when no epileptic seizure wave is detected, the brain wave signal characteristics of epilepsy patients may be distinguished from the brain wave signal characteristics of normal people.

The present disclosure may provide an apparatus and method for determining the state of a driver with epilepsy, with or without seizures, on the basis of the driver's brain wave signal.

FIG. 7 is a block diagram illustrating a configuration of an apparatus for monitoring a driver with epilepsy on the basis of the driver's brain wave signal according to one embodiment of the present disclosure.

Referring to FIG. 7, a monitoring apparatus 700 may include a sensor 710, an analyzer 720 and/or a controller 730. It should be noted, however, that only some of the components necessary for explaining the present embodiment are shown. The components included in the monitoring apparatus 700 are not limited to the above-described embodiment. For example, two or more constituent units may be implemented in one constituent unit, and an operation performed in one constituent unit may be divided and executed in two or more constituent units. Also, some of the constituent units may be omitted or additional constituent units may be added.

According to the present disclosure, a monitoring apparatus and/or method using a brain wave signal may collect a brain wave signal for a driver with epilepsy in a mobility for a predetermined time. In addition, a monitoring apparatus of the present disclosure may determine the driver's state by analyzing the collected brain wave signal. In addition, a monitoring apparatus of the present disclosure may control an operation of the mobility on the basis of the determined state of the driver. Herein, monitoring may mean monitoring a brain wave signal of a driver with epilepsy.

In one embodiment, the monitoring apparatus 700 of the present disclosure may collect a brain wave signal for a driver with epilepsy in a mobility for a predetermined time. In addition, the sensor 710 may perform the operation.

Here, the brain wave signal may mean a brain wave signal at each frequency. In addition, an amplitude of the brain wave signal at each frequency may mean a power of a frequency band within a predetermined range. In other words, the amplitude of the brain wave signal at each frequency may mean a power that is obtained by converting, for example, measured signals by Fourier transform into a frequency band in a frequency domain. In addition, the brain wave signal may be a brain wave signal in a time series plane.

The monitoring apparatus 700 of the present disclosure may determine the driver's state by analyzing the collected brain wave signal. In addition, the analyzer 720 may perform the operation.

Herein, the analysis may include a process of comparing an amplitude of the brain wave signal at each frequency, which is collected for the predetermined time, and a predetermined threshold. In addition, the analysis may include a process of comparing an amplitude of the brain wave signal, which is collected in a time series plane for the predetermined time, and a predetermined threshold. Alternatively, an amplitude of the brain wave signal may mean a power spectrum of the brain wave signal at a specific frequency.

Here, the threshold may be a preset value or a value input by a user. In addition, the threshold may be different for each driver from whom a brain wave signal is collected. For example, it may be a value reflecting the brain wave signal characteristic of each driver. In order to reflect an analysis result of the brain wave signal characteristic, a predetermined learning process may be performed in advance for characteristics displayed in a driver's brain wave signal. In addition, the threshold may have multiple values.

Here, the threshold may be a statistical value of a brain wave signal for which prior learning is performed according to drivers. For example, prior learning may be performed for a brain wave signal of a driver with epilepsy in a normal state. Alternatively, prior learning may be performed for a brain wave signal of a driver with epilepsy in a seizure. Alternatively, prior learning may be performed for brain wave signals of predetermined epileptic patients in seizures. In other words, the brain wave signals of the driver with epilepsy in a seizure may mean a brain wave signal reflecting a brain wave characteristic of a particular individual. The brain wave signals of the predetermined epileptic patients in seizures may mean brain wave signals reflecting the typical brain wave characteristics of epileptic patients. Here, the statistical value may mean an average value, a weighted average value, a maximum value, or a minimum value.

Figure 8:
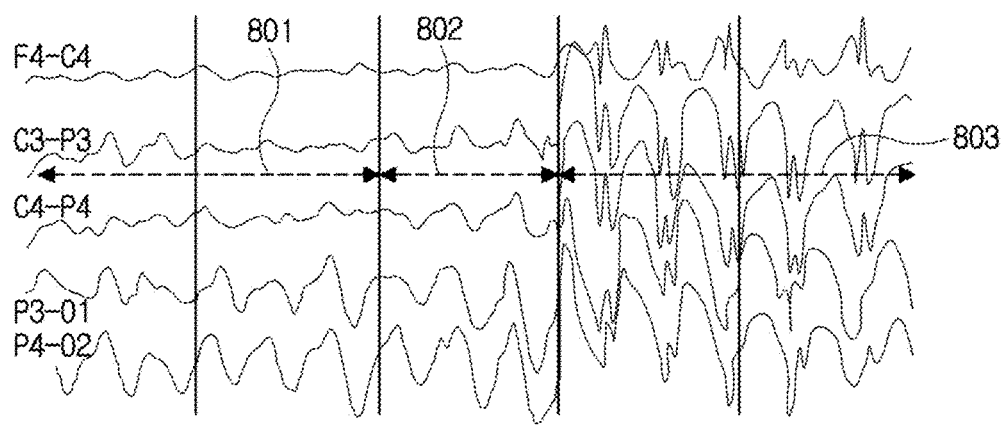
FIG. 8 is a view illustrating a brain wave signal of an epilepsy patient during a seizure according to one embodiment of the present disclosure.

FIG. 8 is a view illustrating a brain wave signal of an epilepsy patient during a seizure according to one embodiment of the present disclosure.

Referring to FIG. 8, respective brain wave signals obtained from predetermined brain wave measurement channels may be distinguished into brain wave signals in a normal state 801, brain wave signals in a transition section 802, and brain wave signals in a seizure 803. Here, the transition section 802 may mean a section where a normal state is replaced by a seizure state. According to brain wave measurement channels, waveforms of brain wave signals in a transition section 802 may have a smaller difference than waveforms of brain wave signals in a normal state 801.

Here, the driver's state may be classified as a predetermined phase on the basis of a normal state 801 or a seizure 803 or both. The phases may be set by a user input or be preset in a mobility.

For example, the driver's state may be determined based on a ratio of a brain wave signal collected from the driver to a brain wave signal of the driver in a normal state 801. Alternatively, the driver's driver may be determined based on a ratio of an amplitude or power spectrum of a brain wave signal collected from the driver to an amplitude or power spectrum of a brain wave signal of the driver in a normal state 801.

For example, the driver's state may be determined based on a ratio of an amplitude or power spectrum of a brain wave signal collected from the driver to an amplitude or power spectrum of a brain wave signal of the driver in a seizure 803.

In another example, the driver's state may be determined based on a ratio of a brain wave signal collected from the driver to a brain wave signal of predetermined epileptic patients in a seizure 803.

Here, the brain wave signal may mean an amplitude or a power spectrum of a brain wave signal.

In one embodiment, for example, when the collected brain wave signal is equal to or greater than 120% of a brain wave signal of the driver in a normal state 801, for which prior learning is performed, the driver's state may be determined as a first state.

In addition, when the collected brain wave signal is equal to or greater than 150% of a brain wave signal of the driver in a normal state 801, for which prior learning is performed, the driver's state may be determined as a second state.

When the collected brain wave signal is equal to or greater than 180% of a brain wave signal of the driver in a normal state 801, for which prior learning is performed, the driver's state may be determined as a third state.

In another embodiment, for example, when the collected brain wave signal is equal to or greater than 30% of a brain wave signal of the driver in a seizure 803, for which prior learning is performed, the driver's state may be determined as a first state.

In addition, when the collected brain wave signal is equal to or greater than 50% of a brain wave signal of the driver in a seizure 803, for which prior learning is performed, the driver's state may be determined as a second state.

When the collected brain wave signal is equal to or greater than 70% of a brain wave signal of the driver in a seizure 803, for which prior learning is performed, the driver's state may be determined as a third state.

The percentage values may be set by a user input or be preset in a mobility.

Meanwhile, the analysis may include a process of extracting a brain wave signal at each frequency.

In addition, a brain wave signal at each frequency that is used for the analysis may be a statistical value of a brain wave signal collected for a predetermined time. In one embodiment, the statistical value may mean an average value, a weighted average value, a maximum value, or a minimum value.

In addition, the analysis may determine a driver's state from a point where an amplitude of a brain wave signal is equal to or greater than a predetermined threshold.

Herein, the analysis may include a process of comparing an amplitude of the brain wave signal at each frequency, which is collected for the predetermined time, and a predetermined threshold.

In addition, the analysis may be performed by using a brain wave signal template for each driver. Herein, a brain wave signal template may mean a brain wave signal in a time domain, which is obtained beforehand within a predetermined time range after the onset of a predetermined state. The state may include a seizure. For example, the analysis may be performed by comparing an amplitude-time graph waveform of a driver's brain wave signal obtained for a predetermined time and the predetermined brain wave signal template. The brain wave signal template may be obtained through a virtual simulation process or through a predetermined learning process.

Here, the comparison may mean determining a similarity between graph waveforms. The similarity determination may apply various conventional methods used in the field of image recognition or classification. Herein, a similarity between brain wave signal characteristics may be expressed by a probability or a numerical value.

In addition, the ready-made brain wave signal template may be scaled in the analysis process. In other words, the amplitude of a brain wave signal graph may be scaled up or down at a predetermined ratio.

For example, in order to obtain and make a similarity between an amplitude-time graph waveform of a driver's brain wave signal collected for a predetermined time and the brain wave signal template be equal to or greater than a first ratio, the size of the brain wave signal template may be decreased at a second ratio.

The first ratio and/or the second ratio may be set by a user input or be preset in a mobility.

For example, when the size of the brain wave signal template is decreased by 30% in order to obtain a similarity of 80% and above between both graph waveforms, the driver's state may be determined as a first state.

For another example, when the size of the brain wave signal template is decreased by 50% in order to obtain a similarity of 80% and above between both graph waveforms, the driver's state may be determined as a second state.

For yet example, when the size of the brain wave signal template is decreased by 70% in order to obtain a similarity of 80% and above between both graph waveforms, the driver's state may be determined as a third state.

Meanwhile, in the case of an analysis based on the brain wave signal template, the brain wave signal template should be obtained using a brain wave signal for a same driver, and the brain wave signal template and the obtained brain wave signal of the driver should be measured in a desirably identical environment.

In addition, the analysis process scaling the above-described brain wave signal template at a predetermined ratio may be similarly applied to an analysis process for a brain wave signal either in a time series plane or at each frequency, which is collected for a predetermined time. In other words, a size of a time series graph for a brain wave signal collected for a predetermined time or a graph size of a brain wave signal at each frequency may be scaled up or down at a predetermined ratio in the analysis process.

The monitoring apparatus 700 of the present disclosure may control an operation of a mobility on the basis of the determined state of a driver with epilepsy. In addition, the controller 730 may perform the operation.

Here, the mobility may include a predetermined apparatus. For example, the predetermined apparatus may include a steering apparatus, an accelerator pedal, a brake pedal, a transmission, an audio guidance system, a navigation system, and other mobility manipulation devices.

For example, when a driver's state is determined as a first state, the speed of a mobility may be limited to a predetermined speed and below. In addition, a power and/or a torque of a mobility may be limited to a predetermined magnitude and below.

For another example, when a driver's state is determined as a second state, the location information of a mobility may be transmitted to a preset user or a preset place (i.e., an emergency room, 911 call center, etc.).

In another example, when a driver's state is determined as a third state, a mobility may be guided to have an emergency stop.

In one embodiment, for example, when a driver's state is determined as a first state, the speed of a mobility may be limited to 60 km/h and below, emergency lights may be turned on, or a voice prompt purporting to stop the mobility may be provided.

In addition, when a driver's state is determined as a second state, the speed of a mobility may be limited to 30 km/h and below, or location information of the mobility and/or a warning about possible seizure may be transmitted to a guardian of the driver or a nearby emergency room. A voice prompt purporting to stop the mobility may also be provided.

In addition, when a driver's state is determined as a third state, a mobility may have an emergency stop, the mobility may be controlled to run at a predetermined speed and below, or location information of the mobility and/or a warning about possible seizure may be transmitted to a guardian of the driver or a nearby emergency room. A voice prompt purporting to stop the mobility may also be provided. For example, the predetermined speed may be 10 km/h.

Meanwhile, when a driver's state changes, the monitoring apparatus 700 of the present disclosure may control a mobility on the basis of the changed state of a driver with epilepsy. In addition, the controller 730 may perform the operation.

For example, when a driver's state changes from the first state to the normal state, a speed-limiting operation or emergency lights of a mobility may be turned off. In other words, an operation of the mobility that has been implemented for the first state may be replaced by an original operation for the normal state.

For another example, when a driver's state changes from the second state to the normal state, a speed-limiting operation or emergency lights of a mobility may be turned off. In other words, an operation of the mobility that has been implemented for the second state may be replaced by an original operation for the normal state.

In another example, when a driver's state changes from the third state to the normal state, a control operation for keeping an emergency stop or emergency lights of a mobility may be turned off. In other words, an operation of the mobility that has been implemented for the third state may be replaced by an original operation for the normal state.

In another example, when a driver's state changes from a predetermined state to the normal state, information that the driver's state has returned to the normal state may be transmitted to a guardian of the driver or a nearby emergency room.

Herein, a change in the driver's state may include a change to the normal state by means of transcranial magnetic stimulation (TMS). Here, the TMS may include repetitive TMS.

Meanwhile, while controlling a mobility by determining a driver's state based on an analysis of the driver's brain wave signal, a monitoring apparatus of the present disclosure may update a predetermined threshold and a predetermined ratio that are used for the analysis. In other words, a brain wave signal of the driver, a determined state of the driver, a mobility control operation, a preset threshold and/or a ratio may be added as learning data in order to set the predetermined threshold and the predetermined ratio.

Figure 9:
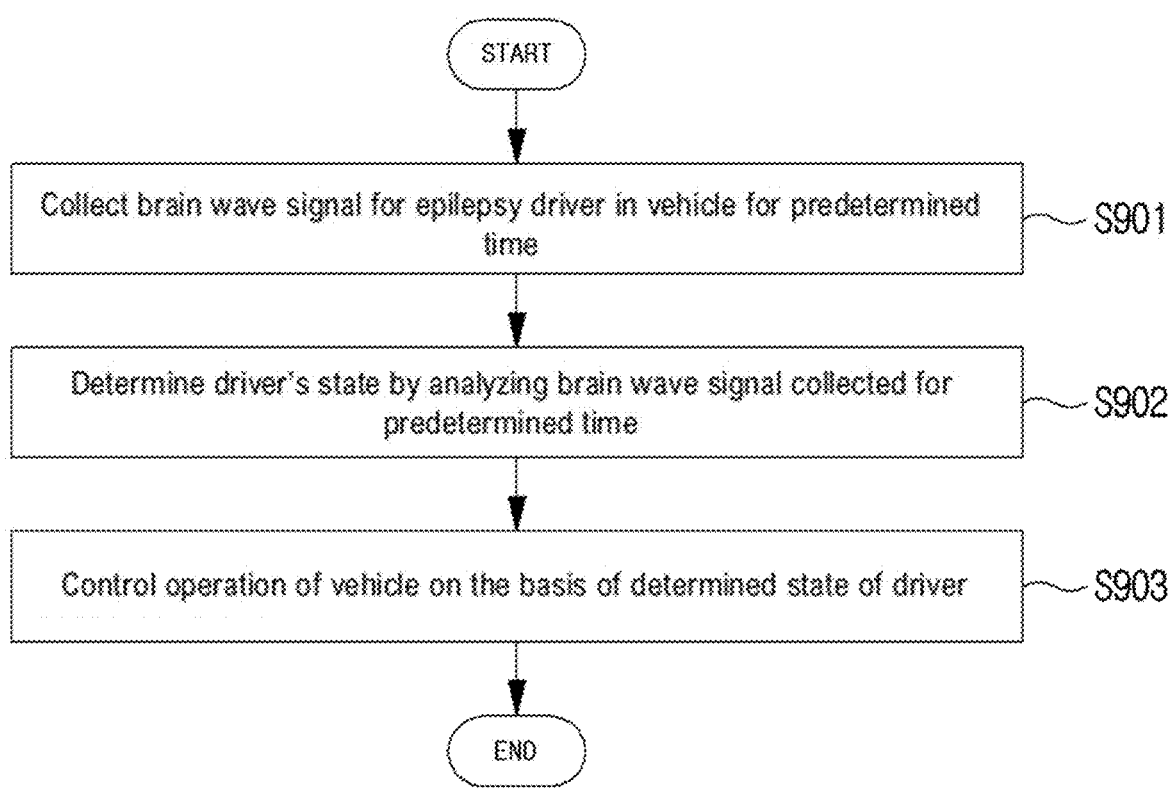
FIG. 9 is a flowchart illustrating a method of operating an apparatus for monitoring a driver with epilepsy according to one embodiment of the present disclosure.

FIG. 9 is a flowchart illustrating a method of operating a monitoring apparatus according to one embodiment of the present disclosure.

In the step S901, a brain wave signal for a driver with epilepsy in a mobility may be collected for a predetermined time.

Here, the brain wave signal may mean a brain wave signal in a time series plane. In addition, the brain wave signal may mean a power spectrum value of brain wave signal at each frequency.

In the step S902, a driver's state may be determined by analyzing a brain wave signal that is collected for the predetermined time.

Here, the analysis may include a process of comparing an amplitude of the brain wave signal, which is collected for the predetermined time, and a predetermined threshold. In addition, the analysis may include a process of comparing an amplitude of a power spectrum of the brain wave signal at each frequency, which is collected for the predetermined time, and a predetermined threshold. In addition, the analysis may be performed by using a brain wave signal template for each driver.

Here, the threshold may be a value obtained based on a learning model that is implemented for at least one of a brain wave signal during the driver's normal state, a brain wave signal during the driver's seizure, and a brain wave signal during a seizure of predetermined epilepsy patients.

Here, the obtained value may be an amplitude or a power spectrum value of a brain wave signal.

Here, the driver's state may be classified as a predetermined phase on the basis of at least one of a normal state and a seizure. In addition, the driver's state may be determined based on a ratio of a brain wave signal collected for the predetermined time to a brain wave signal during the driver's normal state. In addition, the driver's state may be classified into multiple phases on the basis of the ratio. In addition, the driver's state may be determined based on a ratio of a brain wave signal collected for the predetermined time to a brain wave signal during the driver's seizure. In addition, the driver's state may be classified into multiple phases on the basis of the ratio.

Here, the brain wave signal may be an amplitude or a power spectrum value of a brain wave signal.

Here, the ratio may be a value set for monitoring the driver's state.

In the step S903, an operation of a mobility may be controlled on the basis of the determined state of a driver.

Herein, controlling an operation of the mobility may include limiting at least one of speed, power and torque of the mobility to a predetermined value and below on the basis of the determined state of the driver.

In addition, controlling an operation of the mobility may include transmitting location information of the mobility to at least one of a preset user and a preset place on the basis of the determined state of the driver.

In addition, controlling an operation of the mobility may include stopping the mobility on the basis of the determined state of the driver.

In addition, when the driver's state changes to a normal state, controlling an operation of the mobility may include turning off the operation of limiting the speed of the mobility.

Effects obtained in the present disclosure are not limited to the above-mentioned effect, and other effects not mentioned above may be clearly understood by those having ordinary skill in the art from the following description.

Although specific methods of the present disclosure are described as a series of operation steps for clarity of a description, the present disclosure is not limited to the sequence or order of the operation steps described above. The operation steps may be simultaneously performed or may be performed sequentially but in different order. In order to implement the method of the present disclosure, additional operation steps may be added and/or existing operation steps may be eliminated or substituted.

Various forms of the present disclosure are not presented to describe all of available combinations but are presented to describe only representative combinations. Steps or elements in various forms may be separately used or may be used in combination.

In addition, various forms of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (i.e., operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An apparatus for monitoring a driver using a brain wave signal of the driver, the apparatus comprising:
   a sensor configured to collect a brain wave signal for a driver in a vehicle for a predetermined time;
   an analyzer configured to determine a driver's state by analyzing the brain wave signal collected for the predetermined time; and
   a controller configured to control an operation of the vehicle on the basis of the determined driver's state,
   wherein the driver's state is determined to be one of a plurality of abnormal states based on a driver-specific brain wave signal template,
   wherein the driver-specific brain wave signal template is obtained beforehand,
   wherein the driver's state is determined by comparing the brain wave signal collected for the predetermined time and the driver-specific brain wave signal template, and
   wherein the controller differently controls the operation of the vehicle based on each of the plurality of abnormal states.

2. The apparatus of claim 1, wherein the comparing is based on an amplitude waveform of the brain wave signal for the predetermined time and an amplitude waveform of the brain wave signal template.

3. The apparatus of claim 2, wherein the driver's state is determined by determining a similarity between the brain wave signal and brain wave signal template amplitude waveforms.

4. The apparatus of claim 3, wherein the amplitude waveform of the brain wave signal template is scaled up or down for the comparison.

5. The apparatus of claim 1, wherein the controller limits at least one of speed, power, or torque of the vehicle to a predetermined value and below on the basis of the determined driver's state among the plurality of abnormal states.

6. The apparatus of claim 1, wherein the controller transmits location information of the vehicle to at least one of a preset user or a preset place, on the basis of the determined driver's state among the plurality of abnormal states.

7. The apparatus of claim 1, wherein the controller stops the vehicle on the basis of the determined driver's state among the plurality of abnormal states.

8. The apparatus of claim 1, wherein the analyzer is configured to classify each of the plurality of abnormal states based on a corresponding ratio preset in the analyzer.

9. A method of monitoring a driver using a brain wave signal of the driver, the method comprising:
   collecting, by a sensor, a brain wave signal for a driver in a vehicle for a predetermined time;
   determining, by an analyzer, a driver's state by analyzing the brain wave signal collected for the predetermined time; and
   controlling, by a controller, an operation of the vehicle on the basis of the determined driver's state,
   wherein the driver's state is determined to be one of a plurality of abnormal states based on a driver-specific brain wave signal template,
   wherein the driver-specific brain wave signal template is obtained beforehand,
   wherein the driver's state is determined by comparing the brain wave signal collected for the predetermined time and the driver-specific brain wave signal template, and
   wherein the controller differently controls the operation of the vehicle based on each of the plurality of abnormal states.

10. The method of claim 9, wherein the comparing is based on an amplitude waveform of the brain wave signal for the predetermined time and an amplitude waveform of the brain wave signal template.

11. The method of claim 10, wherein the driver's state is determined by determining a similarity between the brain wave signal and brain wave signal template amplitude waveforms.

12. The method of claim 11, wherein the amplitude waveform of the brain wave signal template is scaled up or down for the comparison.

13. The method of claim 9, wherein the controller limits at least one of speed, power, or torque of the vehicle to a predetermined value and below on the basis of the determined driver's state among the plurality of abnormal states.

14. The method of claim 9, wherein the controller transmits location information of the vehicle to at least one of a preset user or a preset place, on the basis of the determined driver's state among the plurality of abnormal states.

15. The method of claim 9, wherein the controller stops the vehicle on the basis of the determined driver's state among the plurality of abnormal states.

16. The method of claim 9, wherein the analyzer is configured to classify each of the plurality of abnormal states based on a corresponding ratio preset in the analyzer.

* * * * *